US010655768B2

(12) United States Patent
Jones et al.

(10) Patent No.: US 10,655,768 B2
(45) Date of Patent: May 19, 2020

(54) BREAKAWAY CONNECTOR

(71) Applicant: Site Saver, Inc., Fayetteville, AR (US)

(72) Inventors: Spencer A. Jones, Conway, AR (US); Jordan Mykleby, Fayetteville, AR (US); Vance Clement, Fayetteville, AR (US); David Eddy, Indianapolis, IN (US)

(73) Assignee: Site Saver, Inc., Fayetteville, AR (US)

( * ) Notice: Subject to any disclaimer, the term of this patent is extended or adjusted under 35 U.S.C. 154(b) by 0 days.

(21) Appl. No.: 15/237,607

(22) Filed: Aug. 15, 2016

(65) Prior Publication Data
US 2017/0067586 A1    Mar. 9, 2017

Related U.S. Application Data

(60) Provisional application No. 62/204,845, filed on Aug. 13, 2015.

(51) Int. Cl.
F16L 29/04       (2006.01)
A61M 39/22       (2006.01)
(Continued)

(52) U.S. Cl.
CPC ............ F16L 29/04 (2013.01); A61M 39/06 (2013.01); A61M 39/10 (2013.01); A61M 39/22 (2013.01);
(Continued)

(58) Field of Classification Search
CPC ............... A61M 39/26; A61M 39/105; A61M 2039/1033; A61M 39/24; A61M 39/22;
(Continued)

(56) References Cited

U.S. PATENT DOCUMENTS 3,794,057 A * 2/1974 Badger ............... F16K 17/36
                                          137/614.02
3,797,510 A * 3/1974 Torres ................. F16K 17/36
                                          137/614.04
(Continued)

FOREIGN PATENT DOCUMENTS

WO    2005004974 A1    1/2005
WO    2006122406 A1   11/2006
(Continued)

OTHER PUBLICATIONS

International Search Report and Written Opinion for PCT/US2016/047110, dated Nov. 17, 2016, 11 pages.
(Continued)

Primary Examiner — William M McCalister
Assistant Examiner — Patrick C Williams
(74) Attorney, Agent, or Firm — Waller Lansden Dortch & Davis, LLP; Matthew C. Cox

(57) ABSTRACT

A breakaway connector apparatus for joining a first tubing section to a second tubing section includes a first member and a second member positioned axially opposite the first member. The second member includes a male portion extending from the second member. A housing is disposed between the first and second members, the housing including a socket shaped to receive the male portion of the second member. An axial passage provides a flow path defined inside the housing between the first and second members. A stem is disposed in the axial passage between the first and second members. A first valve is disposed on the first or second member, and the stem engages the first valve and opens the first valve to allow flow between the first and second members through the axial passage when the male portion of the second member is fully received in the socket of the housing.

14 Claims, 11 Drawing Sheets

(51) Int. Cl.
*A61M 39/06* (2006.01)
*A61M 39/24* (2006.01)
*A61M 39/10* (2006.01)
*F16K 17/40* (2006.01)

(52) U.S. Cl.
CPC ............ *A61M 39/24* (2013.01); *F16K 13/04* (2013.01); *Y10T 137/87973* (2015.04)

(58) Field of Classification Search
CPC ........ A61M 39/06; A61M 39/10; F16L 37/30; F16L 29/04; F16K 13/04
See application file for complete search history.

(56) References Cited

U.S. PATENT DOCUMENTS

| | | | |
|---|---|---|---|
| 4,340,049 A | 7/1982 | Munsch | |
| 4,386,622 A | 6/1983 | Munsch | |
| 4,614,201 A * | 9/1986 | King | F16K 17/40 137/312 |
| 4,722,725 A | 2/1988 | Sawyer et al. | |
| 4,827,977 A * | 5/1989 | Fink, Jr. | F16K 17/36 137/614.04 |
| 4,872,471 A | 10/1989 | Schneider | |
| 5,070,905 A | 12/1991 | Paradis | |
| 5,190,067 A | 3/1993 | Paradis | |
| 5,215,538 A | 6/1993 | Larkin | |
| 5,320,390 A | 6/1994 | Kodama et al. | |
| 5,357,998 A * | 10/1994 | Abrams | F16L 55/005 137/614.04 |
| 5,364,371 A | 11/1994 | Kamen | |
| 5,405,339 A | 4/1995 | Kohnen et al. | |
| 5,465,938 A | 11/1995 | Werge | |
| 5,492,147 A | 2/1996 | Challender et al. | |
| 5,535,785 A | 7/1996 | Werge | |
| 5,775,671 A | 7/1998 | Cote, Sr. | |
| 5,820,614 A * | 10/1998 | Erskine | A61M 5/16831 604/533 |
| 5,848,997 A | 12/1998 | Erskine et al. | |
| 5,954,313 A | 9/1999 | Ryan | |
| 6,039,302 A | 3/2000 | Cote, Sr. | |
| 6,146,374 A | 11/2000 | Erskine et al. | |
| 6,546,947 B2 * | 4/2003 | Abrams | F16K 17/406 137/312 |
| 6,585,229 B2 | 7/2003 | Cote, Sr. | |
| 6,655,655 B1 | 12/2003 | Matkovich et al. | |
| 6,755,391 B2 | 6/2004 | Newton | |
| 6,869,426 B2 | 3/2005 | Ganem | |
| 6,883,778 B1 | 4/2005 | Newton | |
| 6,892,998 B2 | 5/2005 | Newton | |
| 7,014,169 B2 | 3/2006 | Newton | |
| 7,100,890 B2 | 9/2006 | Cote, Sr. | |
| 7,153,296 B2 | 12/2006 | Mitchell | |
| 7,357,792 B2 | 4/2008 | Newton | |
| 7,396,348 B2 | 7/2008 | Newton | |
| 7,753,892 B2 | 7/2010 | Newton | |
| 7,766,039 B2 | 8/2010 | Zuck | |
| 7,789,864 B2 | 9/2010 | Cote, Sr. | |
| 7,815,168 B2 | 10/2010 | Vangsness | |
| 7,837,658 B2 | 11/2010 | Cote, Sr. | |
| 7,857,284 B2 | 12/2010 | Kimball | |
| 7,879,012 B2 | 2/2011 | Kane | |
| 7,887,519 B2 | 2/2011 | Cote, Sr. | |
| 7,914,502 B2 | 3/2011 | Newton | |
| 7,955,317 B2 | 6/2011 | Fournie | |
| 7,959,192 B2 | 6/2011 | Elton et al. | |
| 8,002,755 B2 | 8/2011 | Vangsness | |
| 8,100,868 B2 | 1/2012 | Newton | |
| 8,100,869 B2 | 1/2012 | Vangsness | |
| 8,211,069 B2 | 7/2012 | Fangrow, Jr. | |
| 8,529,524 B2 | 9/2013 | Newton | |
| 8,568,371 B2 | 10/2013 | Siopes | |
| 8,795,256 B1 | 8/2014 | Smith | |
| 8,876,784 B2 | 11/2014 | Cote, Sr. | |
| 8,968,261 B2 | 3/2015 | Kimball | |
| 8,974,437 B2 | 3/2015 | Williams et al. | |
| 9,138,572 B2 | 9/2015 | Zeytoonian | |
| 9,259,565 B2 | 2/2016 | Siopes | |
| 9,604,047 B2 | 3/2017 | Newton | |
| 9,849,274 B2 | 12/2017 | Siopes | |
| 9,861,805 B2 | 1/2018 | Dennis et al. | |
| 2001/0042850 A1 | 11/2001 | Cote, Sr. | |
| 2002/0002351 A1 | 1/2002 | Cote, Sr. | |
| 2002/0153503 A1 | 10/2002 | Newton | |
| 2003/0050610 A1 | 3/2003 | Newton | |
| 2003/0085372 A1 | 5/2003 | Newton | |
| 2003/0093061 A1 | 5/2003 | Ganem | |
| 2004/0133171 A1 | 7/2004 | Newton | |
| 2004/0138626 A1 | 7/2004 | Cote, Sr. | |
| 2004/0206924 A1 | 10/2004 | Newton | |
| 2005/0015075 A1 | 1/2005 | Wright et al. | |
| 2005/0038397 A1 | 2/2005 | Newton | |
| 2005/0101939 A1 | 5/2005 | Mitchell | |
| 2005/0165365 A1 | 7/2005 | Newton | |
| 2006/0089605 A1 | 4/2006 | Fitzgerald | |
| 2006/0129109 A1 | 6/2006 | Shaw et al. | |
| 2006/0264841 A1 | 11/2006 | Cote, Sr. | |
| 2006/0293629 A1 | 12/2006 | Cote, Sr. | |
| 2007/0066965 A1 | 3/2007 | Coambs et al. | |
| 2007/0235674 A1 | 10/2007 | Vangsness | |
| 2007/0235675 A1 | 10/2007 | Kimball | |
| 2007/0235676 A1 | 10/2007 | Vangsness | |
| 2007/0238337 A1 | 10/2007 | Kimball | |
| 2007/0255229 A1 | 11/2007 | Kane | |
| 2008/0039802 A1 | 2/2008 | Vangsness | |
| 2008/0197626 A1 | 8/2008 | Coambs et al. | |
| 2009/0209922 A1 | 8/2009 | Boisjoly | |
| 2010/0249725 A1 | 3/2010 | Cote, Sr. | |
| 2010/0249723 A1 * | 9/2010 | Fangrow, Jr. | A61M 39/24 604/247 |
| 2010/0249724 A1 | 9/2010 | Cote, Sr. | |
| 2011/0028915 A1 | 2/2011 | Siopes | |
| 2011/0046573 A1 | 2/2011 | Newton | |
| 2011/0066119 A1 | 3/2011 | Cote, Sr. | |
| 2011/0319859 A1 | 12/2011 | Zeytoonian | |
| 2012/0157933 A1 | 6/2012 | Newton | |
| 2013/0331800 A1 | 8/2013 | Newton | |
| 2014/0031765 A1 | 9/2014 | Siopes | |
| 2015/0157849 A1 | 6/2015 | Phillips et al. | |
| 2016/0114147 A1 | 4/2016 | Siopes | |
| 2017/0000999 A1 | 1/2017 | Dennis et al. | |
| 2017/0067586 A1 | 3/2017 | Jones et al. | |
| 2018/0093086 A1 | 4/2018 | Siopes | |

FOREIGN PATENT DOCUMENTS

| | | |
|---|---|---|
| WO | 2007097985 A2 | 8/2007 |
| WO | 2008054699 A2 | 5/2008 |
| WO | 2014125245 A1 | 8/2014 |
| WO | 2016210300 | 12/2016 |

OTHER PUBLICATIONS

International Search Report and Written Opinion for PCT/US2016/047110, dated Nov. 17, 2016, 11 pages.
International Search Report and Written Opinion for PCT/US2019/014062, dated Apr. 25, 2019, 10 pages.

* cited by examiner

BREAKAWAY CONNECTOR

CROSS-REFERENCES TO RELATED APPLICATIONS

This application claims priority to U.S. Provisional Patent Application No. 62/204,845, all of which is hereby incorporated by reference.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable.

REFERENCE TO SEQUENCE LISTING OR COMPUTER PROGRAM LISTING APPENDIX

Not Applicable.

BACKGROUND

The present disclosure relates generally to devices for connecting tubing for medical applications, and more particularly to break-away valves for connecting tubing.

The introduction of fluids into and out of the body, as well as the placement of devices within the body to capture diagnostics, has long been a standard of care within medical practice. The devices used to accomplish these medically necessary tasks have become more advanced and functionally flexible, they have given the patient the ability to continue activities of daily living while these devices are in place and being used. Instead of having to completely immobilize the patient to facilitate the use of these advanced devices, no immobilization of the patient or a specific limb is required in most cases. This provides many benefits for the patients in terms of the ability to be mobile, perform active therapy, and even leave the hospital setting with these devices still in place and manage their care from home.

Advances in infusion, removal, and diagnostic devices have subsequently led to new risks for these devices during their use. The mobility and state of mind of the patients utilizing such devices has given rise to accidental removal of these carefully placed and delicate devices. These devices are currently secured with different forms of adhesives or sutures, but the failure threshold of these securement devices are limited by the composition of human skin and the amount of surface area available and acceptable for a given patient. These factors have led to adverse events within the medical setting in which catheters, drains, tubes, and other medical devices are inadvertently removed from their intended placement within the patient prior to the intended time of removal.

Accidental removal of these devices is especially dangerous for patients, being that the devices are accessing important veins, arteries, and organs within the patient. The forceful and unintended removal of the devices can cause dermal abrasions, vasculature and arterial tissue damage, organ tissue damage, and in almost every case hemorrhaging of blood from the insertion site.

What is needed then are improvements in devices and methods for preventing accidental or unintentional removal of devices using breakaway connectors for medical tubing.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

The present disclosure includes a breakaway connector device for placement between two existing medical tubing apparatuses. Commonly in currently medical practice, there is a device or tube inserted within the patient that upon exit from the patient's body, presents an apparatus for the connection of an external piece of tubing. The secondary connecting piece of tubing is commonly attached to a container of fluid for infusion, or a container for removal of fluid, sometimes with a pumping mechanism along the tubing in-between the container and the patient. The connection point between these respective medical tubing segments is of utmost importance, as it presents an entry point for pathogens and is usually very close to the patient and therefore near the insertion site.

The present disclosure allows a sealed liquid connection between the two connecting pieces of the medical tubing, but allows a disengagement of the tubing sections from one another once a specific tension threshold is applied. Before the adhesive or securement devices fails, the disclosure "activates" and separates into the two pieces, ultimately preventing the adverse event of premature device removal. The two ends of the devices remaining attached to their respective sides of the tubing serve as protective barriers to external pathogens, and also occludes the flow of fluids to serve as a barrier to fluid leakage out of the patient or ultimately from the containers.

Numerous other objects, advantages and features of the present disclosure will be readily apparent to those of skill in the art upon a review of the following drawings and description of a preferred embodiment.

DETAILED DESCRIPTION

Figure 1:
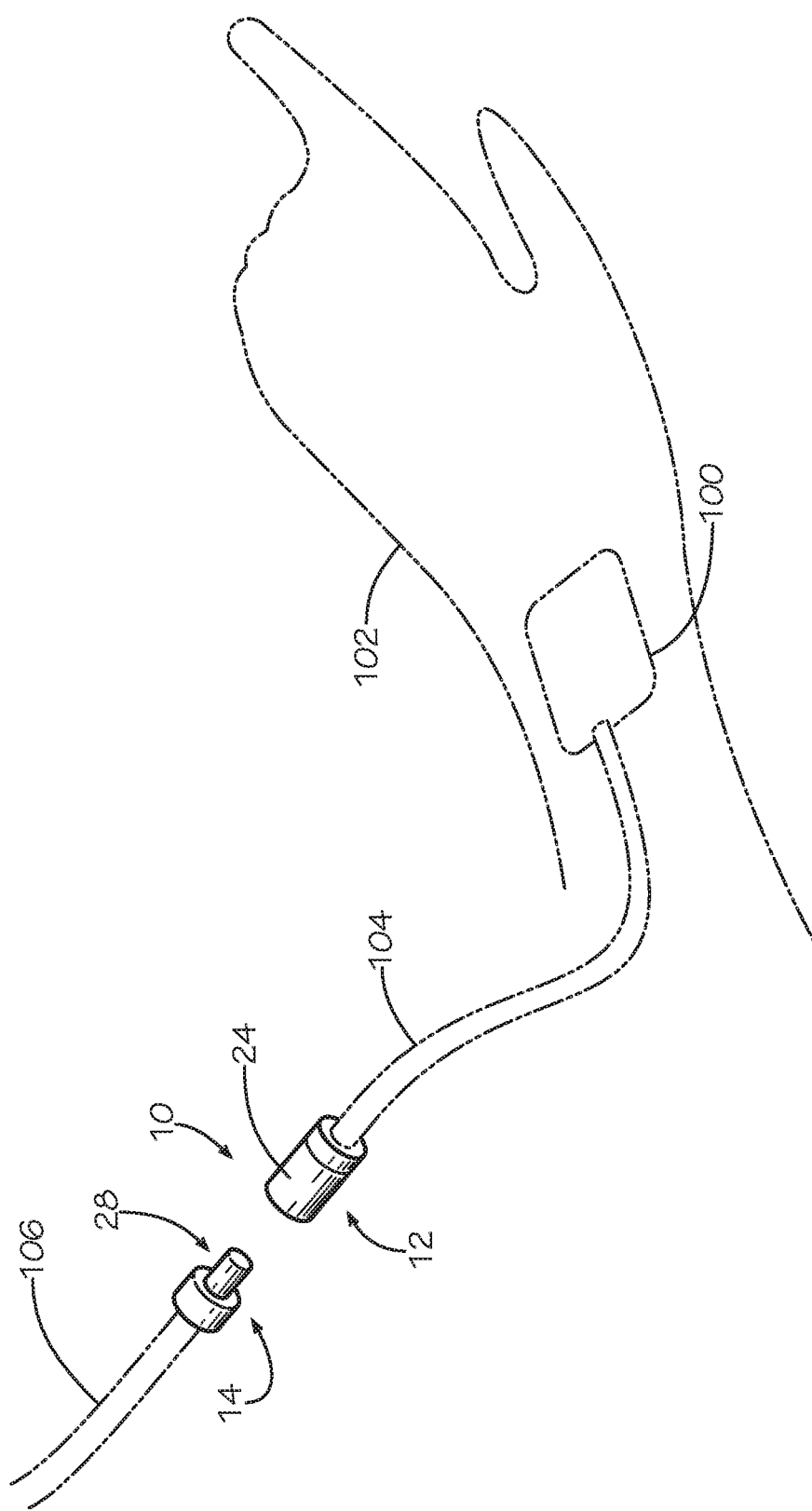
FIG. 1 is a perspective view of an embodiment of a connector of the present disclosure.

While the making and using of various embodiments of the present disclosure are discussed in detail below, it should be appreciated that the present disclosure provides many applicable inventive concepts that are embodied in a wide variety of specific contexts. The specific embodiments discussed herein are merely illustrative of specific ways to make and use the disclosure and do not delimit the scope of the disclosure. Those of ordinary skill in the art will recognize numerous equivalents to the specific apparatus and methods described herein. Such equivalents are considered to be within the scope of this disclosure and are covered by the claims.

In the drawings, not all reference numbers are included in each drawing, for the sake of clarity. In addition, positional terms such as "upper," "lower," "side," "top," "bottom," etc. refer to the apparatus when in the orientation shown in the drawing. A person of skill in the art will recognize that the apparatus can assume different orientations when in use.

Referring further to the drawings, FIG. 1 illustrates an exemplary application of a breakaway connector, or breakaway valve, 10 positioned in a medical tube line. Breakaway connector 10 may be used in any appropriate medical gas, fluid or solid delivery, extraction or monitoring line such as an intravenous (IV) line. Breakaway connector 10 in some embodiments includes a first member 12 and a second member 114. Connector 10 is configured to break apart such that first member 12 separates from second member 14 if a threshold amount of tensile force is applied in opposing axial directions along the connector 10. As seen in FIG. 1, a delivery site 100 such as a catheter or other intravenous needle device is located on a patient 102. A first line 104 extends between connector 10 and delivery site 100. First line 104 includes a free end attached to first member 12. A second line 106 extends between connector 10 and a source or sink for fluid, gas or solid material moving through the line. Second line 106 is attached at a free end to second member 14 in some embodiments. When first and second members 12, 14 are connected, one or more valves within connector 10 are opened to allow fluid, gas and/or solid to travel through connector 10 between first line 104 and second line 106. In the event patient 102 moves in a manner to impart a threshold tensile force on first and second lines 104, 106, connector 10 may separate such that first member 12 becomes disengaged from second member 14. One or more valves in connector 10 may close upon disengagement of first and second members 12, 14 such that flow of fluid, gas or solid is prevented from exiting each of the first and second members 12, 14. In some embodiments, valves in device 10 may be reversed, and the line connected to each member may be opposite the configuration described above.

In some embodiments, connector 10 is designed such that the requisite level of tensile force required to cause first and second members 12, 14 to disengage is sufficiently low to provide disengagement of connector 10 prior to unintentional removal of delivery site 100 from patient 102.

Figure 2:
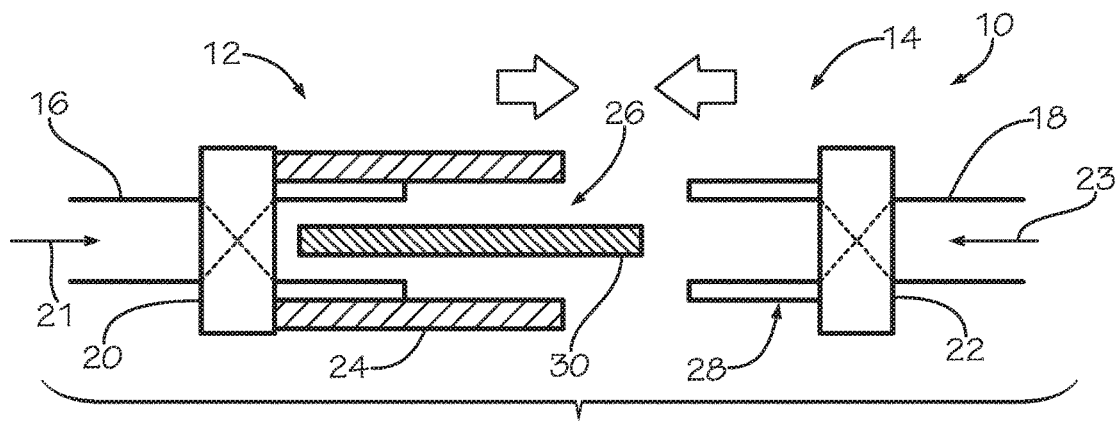
FIG. 2 is a partial exploded cross-section view of an embodiment of a connector of the present disclosure.

Referring to FIG. 2, in some embodiments connector 10 includes a first member 12 and a second member 14 positioned axially opposite first member 12. First member 12 includes a first fitting 16 in some embodiments. First fitting 16 can include any suitable tube or hose fitting configured to engage a corresponding free end of a medical tube. For example, in some embodiments, first fitting 16 can include a hose barb fitting, a female luer fitting, a male luer fitting, a male threaded fitting, a female threaded fitting, or any other suitable fitting. Similarly, second member 14 includes a second fitting 18 in some embodiments. Second fitting 18 can include any suitable tube or hose fitting configured to engage a corresponding free end of a medical tube. For example, in some embodiments, second fitting 18 can include a hose barb fitting, a female luer fitting, a male luer fitting, a male threaded fitting, a female threaded fitting, or any other suitable fitting.

A housing 24 is disposed on first member 12 in some embodiments. Housing 24 can include a tube, cylinder, hose, channel or any suitable structure that provides an axial passage providing a flow path inside the housing between the first and second members. Housing 24 may be a separate piece that is attached to first member 12 in some applications, such as a short section of a hose or tube installed onto a corresponding structure on first member 12, as seen in FIG. 2. Alternatively, housing 24 may be integrally formed on first member 12 in a unitary, one-piece construction such as a single piece of molded or machined material.

Figure 3:
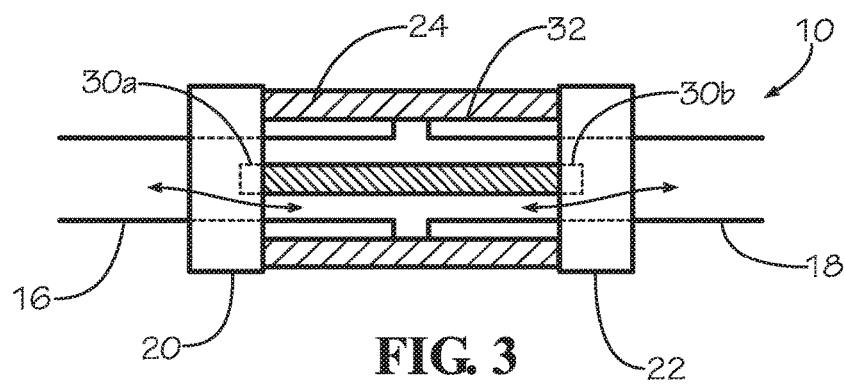
FIG. 3 is a partial exploded cross-section view of an embodiment of a connector of the present disclosure.

Housing 24 defines an open socket 26 positioned and shaped to receive a male portion 28 of second member 14. As seen in FIG. 2 and FIG. 3, a male portion 28 of second member 18 may be inserted into open socket 26, providing a structural attachment between first member 12 and second member 14. Male portion 28 is received in open socket 26 on housing 24 in a friction fit, or an interference joint 32, in some embodiments. In some embodiments, the interior portion of housing 24 that receives male portion 28 includes a substantially smooth interior wall such that male portion 28 slides into and out of housing 24. Interference joint 32 provides a liquid-tight seal between housing 24 and male portion 28 in some embodiments. Interference joint 32 also provides a gas-tight seal between housing 24 and male portion 28 in some embodiments.

At least one check valve 20 is disposed on first member 12 or second member 14 in some applications. The check valve is operable to allow flow of fluid or gas in a first flow direction, but to restrict or stop the flow of fluid or gas in the opposite flow direction. Check valve 20 is disposed on first member 12 in some embodiments. First check valve 20 is generally operable to stop the flow of fluid and/or gas in first flow direction 21 when first check valve 20 is closed. Similarly, in some embodiments, a second check valve 22 is disposed on second member 14. Second check valve is generally operable to stop the flow of fluid and/or gas in second flow direction 23 when second check valve 22 is closed. As seen in FIG. 2, when the connector 10 is in a disengaged state, both first and second check valves 20, 22 are closed thereby preventing liquid and/or gas from travelling through the space between the first and second members 12, 14. In some embodiments, first and second valves 20, 22 may be described as one-way valves or check valves.

Figure 4:
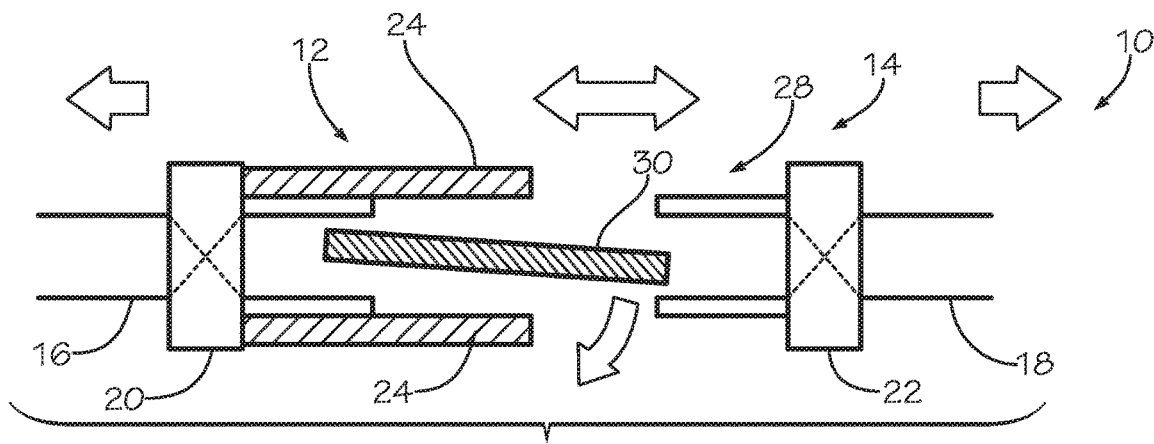
FIG. 4 is a partial exploded cross-section view of an embodiment of a connector of the present disclosure.

A moveable stem 30 is positioned in the axial passage in housing 24 between first and second members. Stem 30 includes a rigid member with an outer diameter less than the inner diameter of the axial passage inside housing 24 providing a flow path between first and second members. Stem 30 includes a solid elongated member in some embodiments. Stem 30 has a length greater than the axial distance between first valve 20 and second valve 22 when male portion 28 is fully seated in housing 24 in some embodiments. As such, stem 30 is axially compressed between first valve 20 and second valve 22, causing first stem end 30*a* to engage first valve 20 and second stem end 30*b* to engage second valve 22, as seen in FIG. 3. This condition is present when first and second members 12, 14 are in a fully-seated position relative to housing 24. In this condition, which may be referred to as an engaged position for connector 10, first stem end 30*a* applies force against first valve 20, causing first valve 20 to slightly open. The opening of first valve 20 by first stem end 30*a* allows fluid, gas and/or solid to travel from first fitting 16 into the axial passage defined by housing 24. At the same time, second stem end 30*b* applies force against second valve 22, causing second valve 22 to also slightly open. The opening of second valve 22 by second stem end 30*b* allows fluid, gas and/or solid to travel between second fitting 18 and the axial passage defined by housing 24 between first and second members 12, 14. In the engaged position, as seen in an embodiment in FIG. 3, fluid, gas and/or solid may pass from first connector 16 to second connector 18 through the axial passage defined by housing 24 between first member 12 and second member 14. The friction between male end 28 and housing 24 provides sufficient force to maintain a mechanical attachment between the first and second members 12, 14 via housing 24. As long as the engagement between male end 28 and housing 24 is maintained, stem 30 resides in a position to simultaneously hold both first and second valves 20, 22 in an open position. However, in the event a patient pulls on a tube connected to either first or second fittings 16, 18 (or both), the imparted tensile force may be sufficient to pull male end 28 out of the open socket 26 on housing 24, as seen in FIG. 4. In such an event, stem 30 will be released from its engagement with first and second valves 20, 22, thereby allowing first and second valves 20, 22 to each return to its original bias closed state. As such, connector 10 is modified to a disengaged state, as seen in FIG. 4, and first and second valves 20, 22 are each again closed following the release of stem 30.

Figure 5:
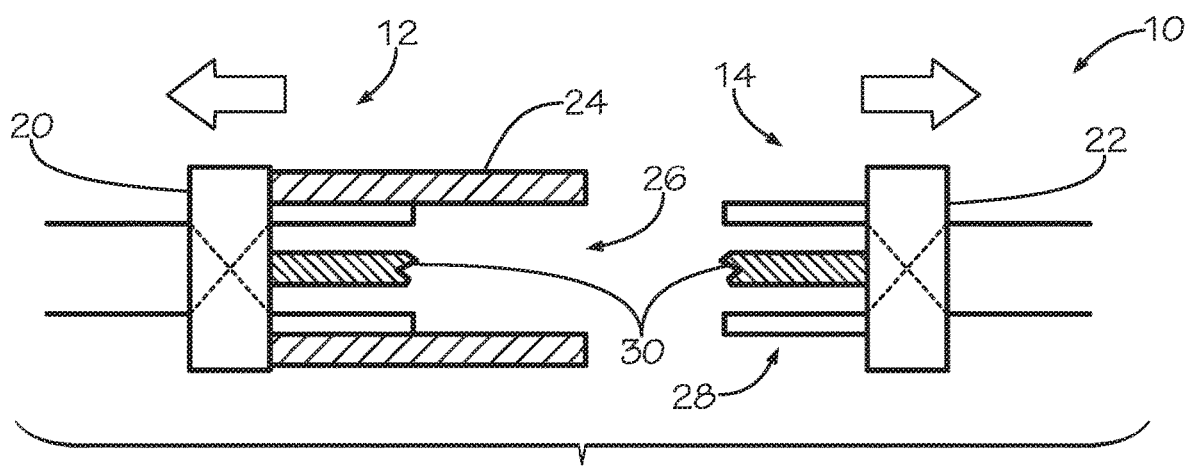
FIG. 5 is a partial exploded cross-section view of an embodiment of a connector of the present disclosure.

When connector 10 is moved to a disengaged state due to a tensile event, as seen for example in FIG. 4, stem 30 may be released from its position in housing 24. In some applications, it is desirable to provide a connector 10 configured as a single-use connector. As such, it may be desirable to disable connector 10 from being re-engaged with a continuous flow path following a tensile event disengagement. For example, following a tensile event disengagement, a user may try to recover stem 30 and position stem 30 in a position in the axial passage in housing 24 to re-assemble connector 10 in an engaged state. However, once connector 10 has become disengaged, portions of the connector may no longer be sufficiently sterile, and it is undesirable to allow patients or users to re-assemble the connector in a second engaged state. Specifically, once stem 30 has fallen out it may be contaminated and should not be used again to re-assemble the connector. In some embodiments, the present disclosure provides a connector 10, as seen in FIG. 5, that includes a frangible stem 30. Frangible stem 30 may be positioned in the axial passage in housing 24 in an engaged state of connector 10 as described above. Upon a tensile event disengagement, however, frangible stem 30 breaks into at least two stem portions. A first stem portion may be retained with first member 12, and a second stem portion may be retained with second member 14, as seen in FIG. 5. Following the break of frangible stem 30, a user will be unable to mechanically re-assemble the connector 10 in an engaged state because the stem is broken.

Figure 6:
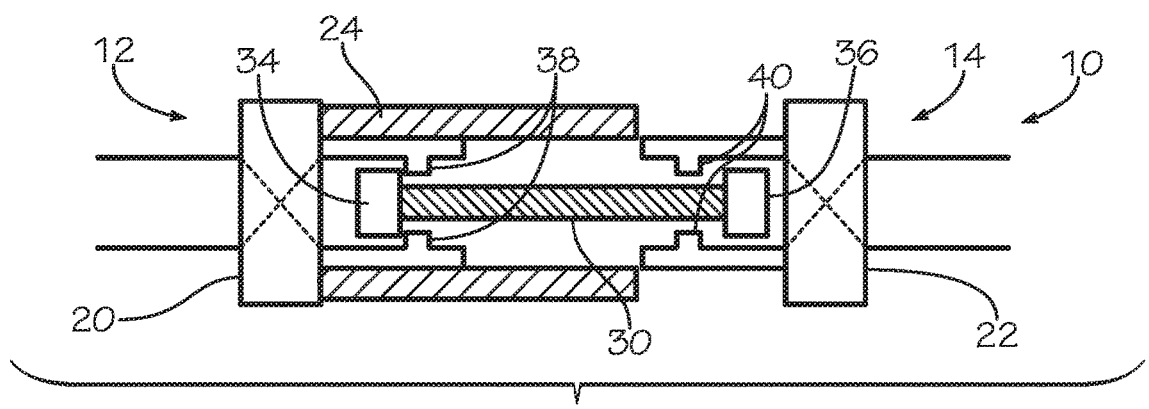
FIG. 6 is a partial exploded cross-section view of an embodiment of a connector of the present disclosure.

Referring to FIG. 6, in some embodiments, stem 30 does not directly engage first valve 20 and second valve 22. Instead, stem 30 engages a first stem carrier 34 positioned at a first axial end of the stem, and a second stem carrier 36 positioned at a second axial end of the stem. First stem carrier 34 includes a moveable member located between first and second members 12, 14 inside the axial passage defined by housing 24. First stem carrier 34 is moveable toward first valve 20. First stem carrier 34 in some embodiments is rigidly fixed to stem 30 using any suitable fixture means such as a mechanical fit or an adhesive. Second stem carrier 36 includes a moveable member located between first and second members 12, 14 inside the axial passage defined by housing 24. Second stem carrier 36 is moveable toward second valve 22. Second stem carrier 36 in some embodiments is rigidly fixed to stem 30 using any suitable fixture means such as a mechanical fit or an adhesive.

Figure 7:
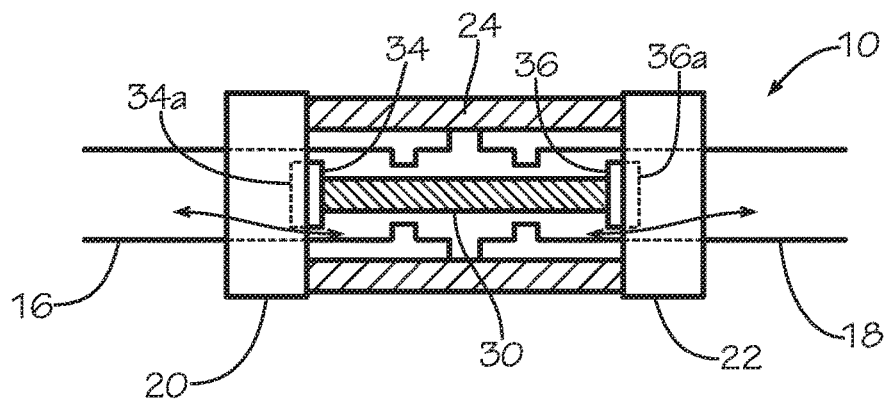
FIG. 7 is a partial cross-section view of an embodiment of a connector of the present disclosure.

When first and second members 12, 14 are arranged in a fully-seated position relative to housing 24, first and second stem carriers 34, 36 and stem 30 are all axially compressed between first and second valves 20, 22 such that first stem carrier 34 engages first valve 20 and second stem carrier 36 engages second valve 22, as seen in FIG. 7. When this occurs, connector 10 attains an engaged state and a continuous flow path is established between first and second connectors 16, 18 because first stem carrier 34 slightly opens first valve 20 and second stem carrier 36 slightly opens second valve 22. Upon a tensile event disengagement, first stem carrier 34 may move away from first valve 20 and/or second stem carrier 36 may move away from second valve 22, thereby stopping the flow of material into the axial passage between the first and second members 12, 14. As seen in FIG. 6, in some embodiments, a first carrier stop 38 is positioned on first member 12 to restrict the axial travel of first stem carrier 34 away from first valve 20. Similarly, in some embodiments, a second carrier stop 40 is positioned on second member 14 to restrict the axial travel of second stem carrier 36 in away from second valve 22. During a tensile event disengagement, first and second carrier stops 38, 40 are operable to stop the travel of the first and second stem carriers 34, 36, respectively, which may impart a tensile force on stem 30. In some embodiments, stem 30 is configured as a frangible stem such that the stem breaks when first and second stem carriers 34, 36 engage first and second carrier stops 38, 40 during tensile event disengagement. First carrier stop 38 in some embodiments includes an annular ring protruding radially inwardly from the interior wall of housing 24. In other embodiments, first carrier stop 38 includes an annular ring protruding radially inwardly from the interior wall of a fixture protruding from first member 12 upon which housing 24 is mounted. Similarly, in some embodiments, second carrier stop 40 includes an annular ring protruding radially inwardly from the interior wall of first male member 28 protruding from second member 14, as seen in FIG. 6.

Figure 8:
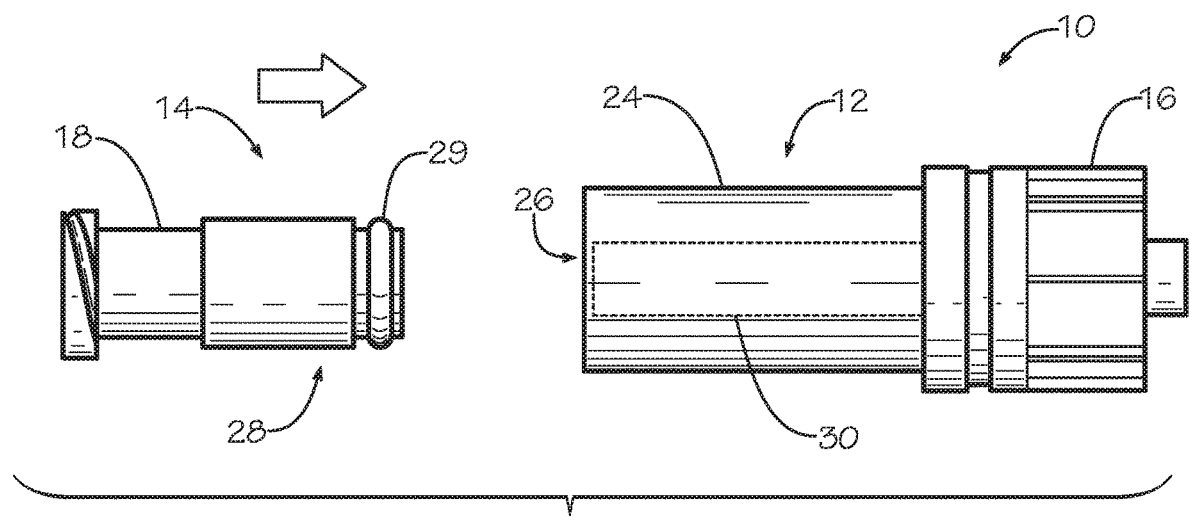
FIG. 8 is a partial exploded view of an embodiment of a connector of the present disclosure.
Figure 9:
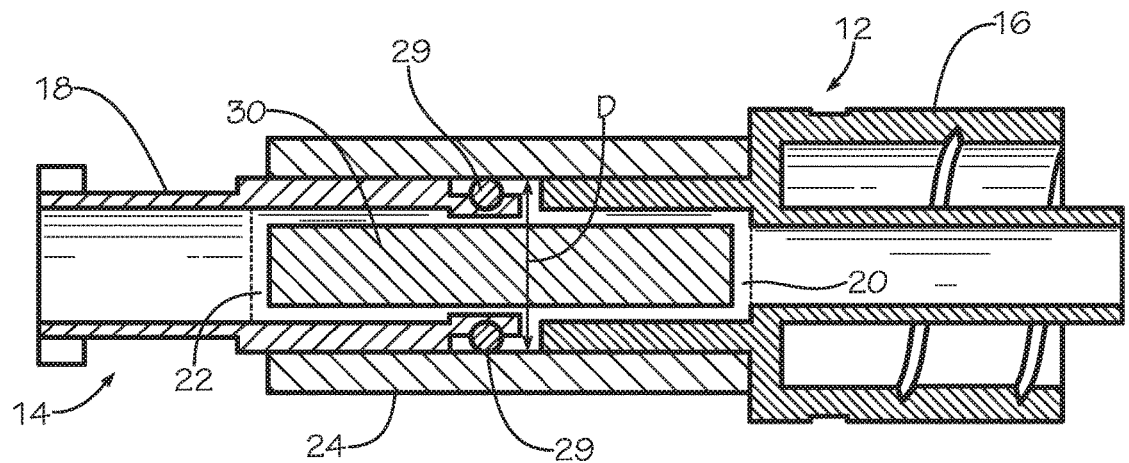
FIG. 9 is a partial exploded cross-section view of an embodiment of a connector of the present disclosure.

Referring to FIGS. 8 and 9, in some embodiments, housing 24 includes an inner diameter D, and male portion 28 includes an O-ring 29 which forms the outer diameter of the male portion. In some embodiments, the outer diameter of the male portion 28 due to O-ring 29 is greater than the inner diameter D such that the O-ring 29 is radially compressed upon insertion of male portion 28 into the open socket on housing 24. As such, the male portion 28 forms an interference fit with housing 24. O-ring 29 may be dimensioned in such a way to influence the required tensile force required to disengage connector 10. For example, when O-ring 29 includes a greater O-ring diameter, the effective outer diameter of male portion 28 increases, causing a more forceful interference fit between male portion 28 and housing 24. This results in a greater tensile force required for a tensile event disengagement of connector 10. Thus, by selecting the diameter of O-ring 29, a user may be able to "tune" the connector 10 to control the requisite level of tensile force required for disengagement of connector 10. In some embodiments, the present disclosure provides a method of matching a breakaway connector to a desired application by providing a connector having a first member and a second member, wherein the first member includes a male portion to be selectively received in a corresponding housing opening on the second member. The method also includes providing first and second O-rings of different material diameters for independent installation on the male portion. The method further includes selecting the first O-ring for placement on the male portion for a first desired tensile disengagement force, and selecting the second O-ring for placement on the male portion for a second desired tensile disengagement force, wherein the first and second tensile disengagement forces are different. The method further includes placing the selected O-ring on the male portion, and inserting the male portion in the socket such that the O-ring is at least partially compressed by the inner wall of the housing.

Figure 10:
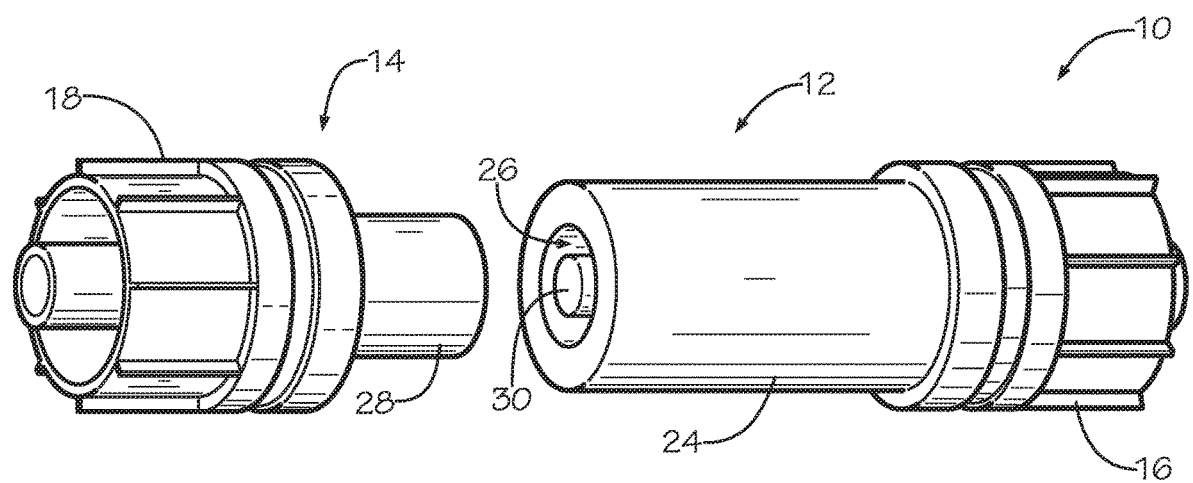
FIG. 10 is a partial exploded cross-section view of an embodiment of a connector of the present disclosure.
Figure 11:
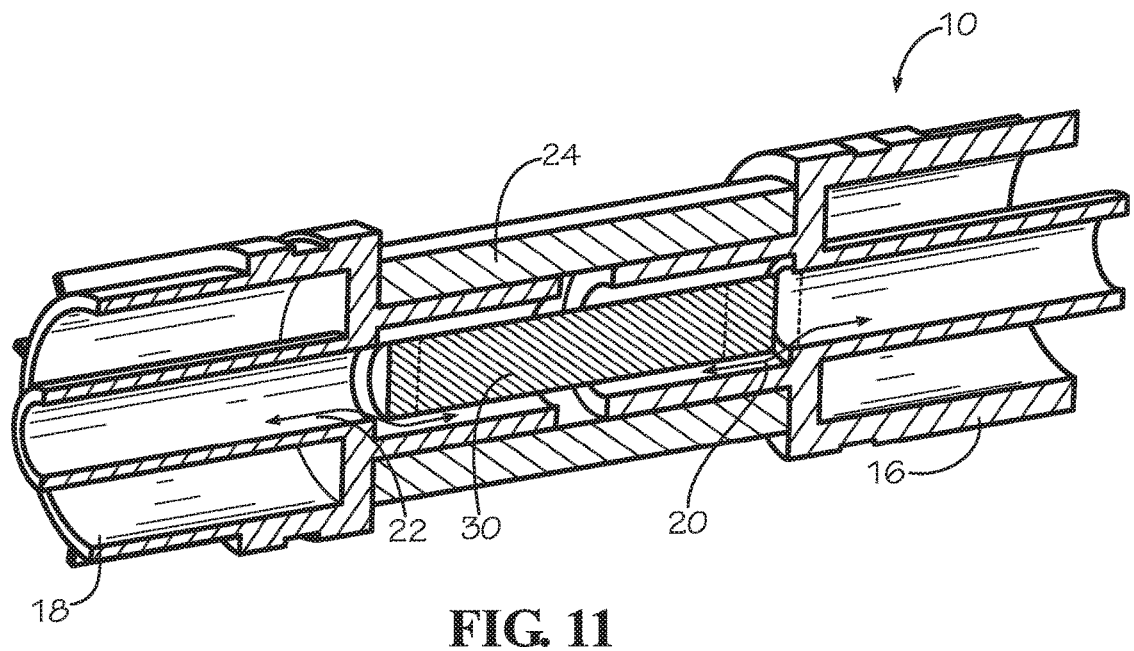
FIG. 11 is a partial exploded cross-section view of an embodiment of a connector of the present disclosure.
Figure 12A:
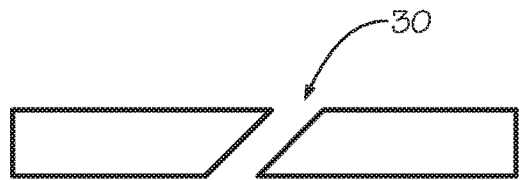
FIGS. 12a-12f are schematics of various embodiments of stems in accordance with the present disclosure.
Figure 12B:
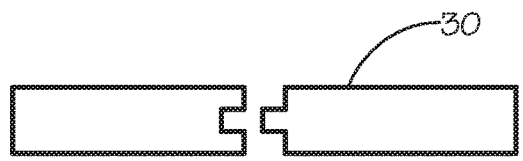
Figure 12C:
Figure 12D:
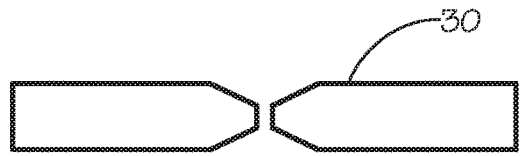
Figure 12E:
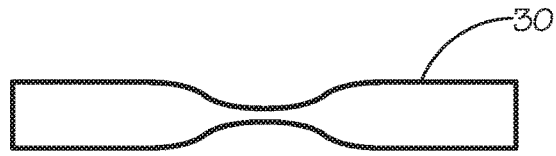
Figure 12F:
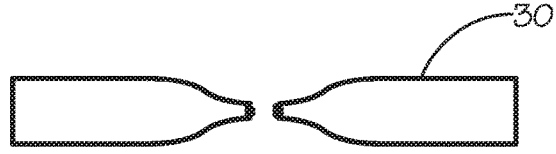
Figure 13:
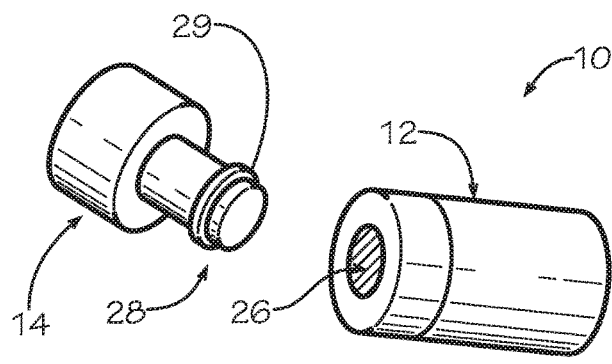
FIG. 13 is a partial exploded perspective view of an embodiment of a connector of the present disclosure.
Figure 14:
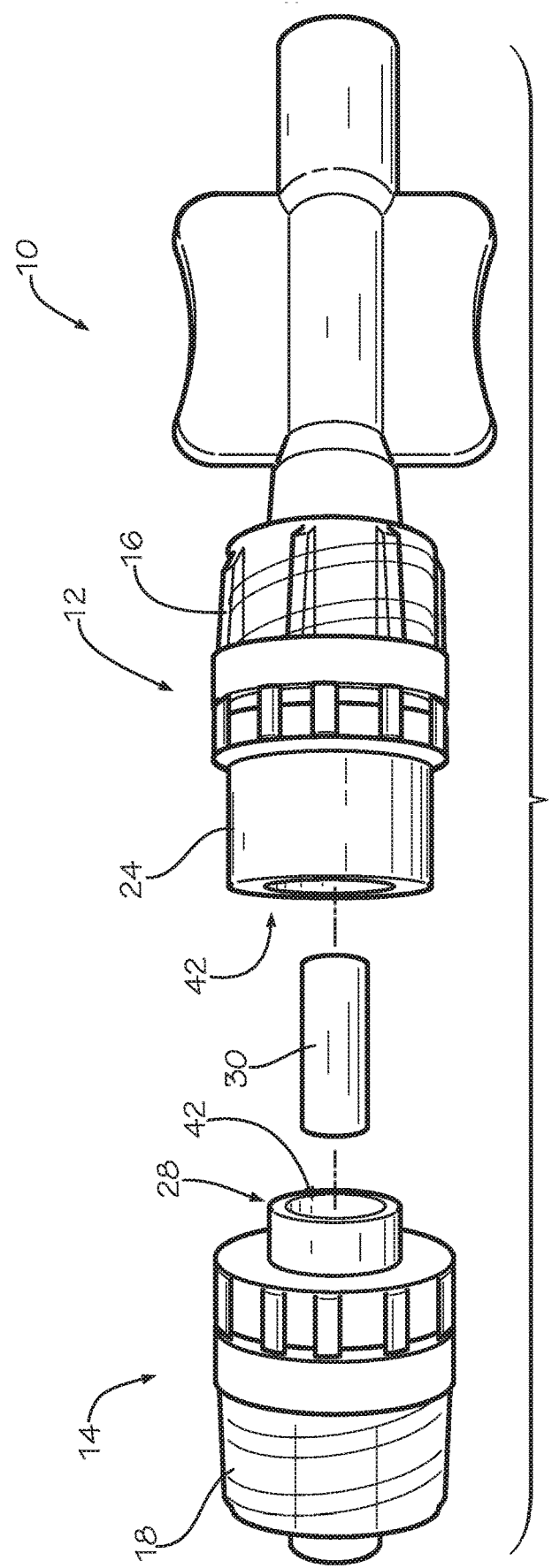
FIG. 14 is a partial exploded perspective view of an embodiment of a connector of the present disclosure.
Figure 15:
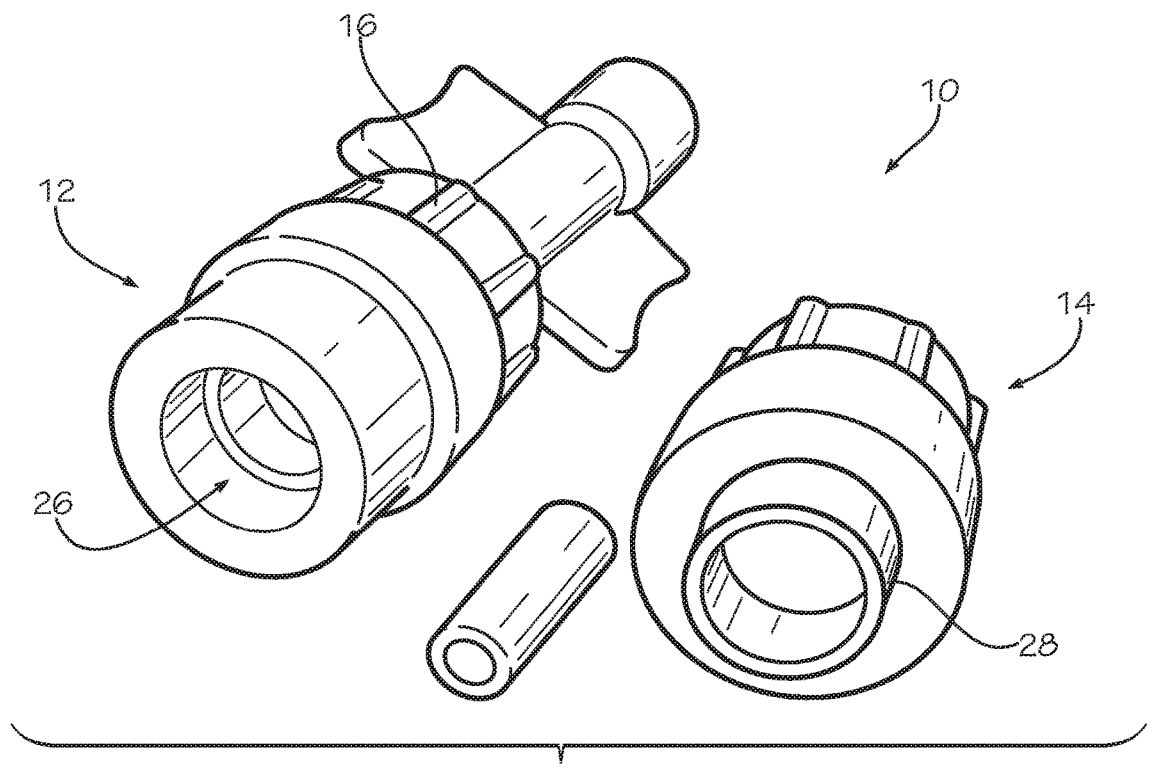
FIG. 15 is a partial exploded perspective view of an embodiment of a connector of the present disclosure.
Figure 16:
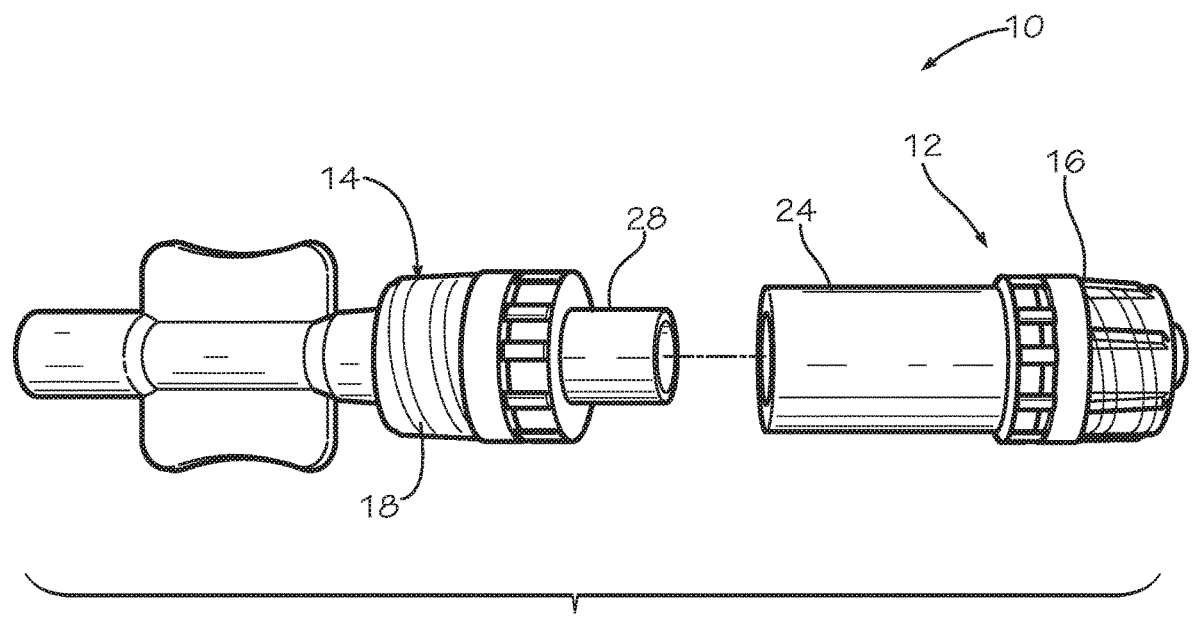
FIG. 16 is a partial exploded perspective view of an embodiment of a connector of the present disclosure.

As seen in FIGS. 10 and 11, in some embodiments, connector 10 includes female luer fittings as first fitting 16 and second fitting 18. In other embodiments, connector 10 includes two male luer fittings for first fitting 16 and second fitting 18. In other embodiments, connector 10 includes one male luer fitting, and one female luer fitting. In some embodiments, first valve 20 and/or second valve 22 include one-way valves, also referred to as check valves, manufactured by Qosina of Edgewood, N.Y. Other suitable one-way or two-way valves may be used for first valve 20 and/or second valve 22 in various embodiments.

Referring further to FIGS. 12a to 12f, various embodiments of frangible stems 30 are shown. Stem 30 may break in a variety of different shapes or locations. Frangible stem 30 is inoperable to open the first valve to allow flow between the first and second members 12, 14 through the axial passage 42 when the frangible stem 30 is broken, in some embodiments.

Referring to FIGS. 13-16, male portion 28 is shown extending from second member 14 for insertion in socket 26 on first member 12. A seal 29 is positioned on male portion 28 in some embodiments. Stem 30 is located between first and second member 12, 14, as shown in the exploded views in FIGS. 14 and 15 in some embodiments.

Figure 17:
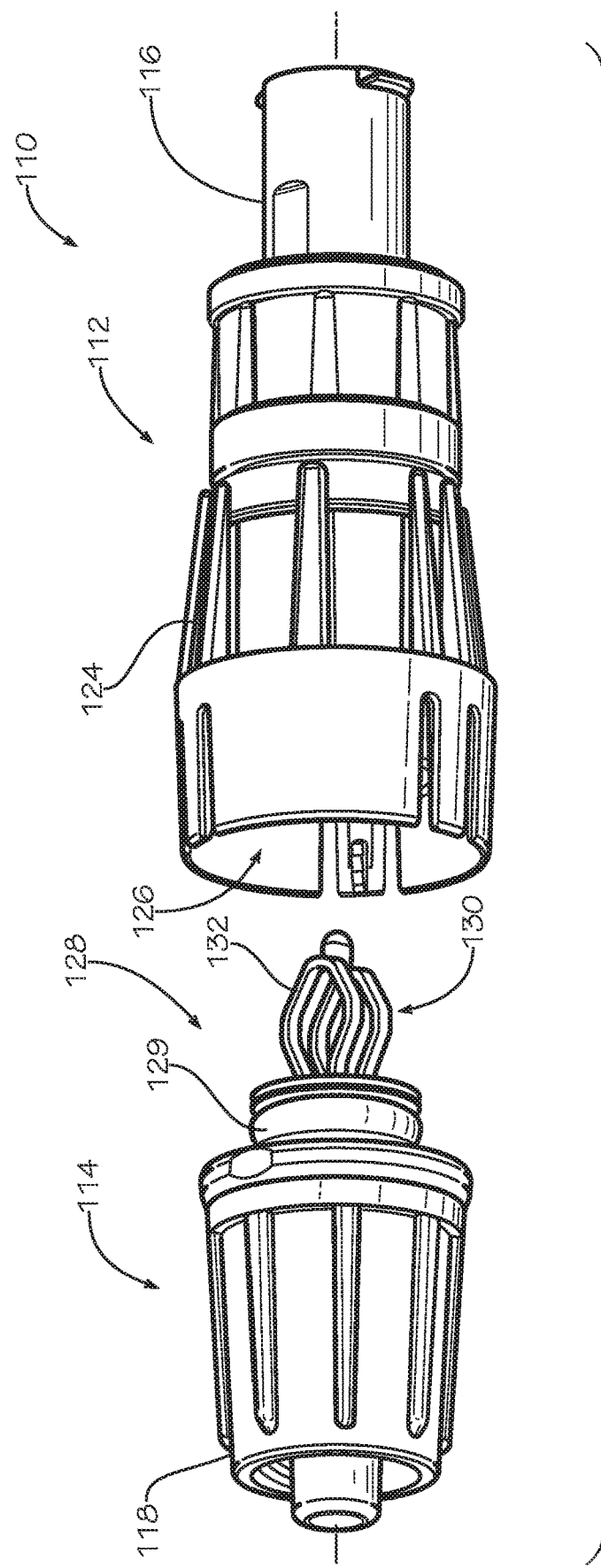
FIG. 17 is a partial exploded perspective view of an embodiment of a connector of the present disclosure.

Referring now to FIG. 17, an alternative embodiment of a breakaway valve 100, or connector, is shown. Valve 100 includes a first member 112 and a second member 114 positioned axially opposite the first member 112. The second member 114 includes a male portion 128 extending from the second member 114 toward the first member 112. A housing 124 is disposed between the first and second members 112, 114. Housing 124 includes a socket 126, shown in FIG. 18 shaped to receive the male portion 128 of second member 114. An axial passage 140 is defined between the first and second members 112, 114 defining a flow path inside the housing 124 between the first and second members 112, 114. A stem 130 is disposed in the axial passage 140 between the first and second members. Stem 130 may be attached to male portion 120 on second member 114 in some embodiments, as seen in FIG. 17. In other embodiments in accordance with this disclosure, stem 130 is positioned in other configurations.

Figure 18:
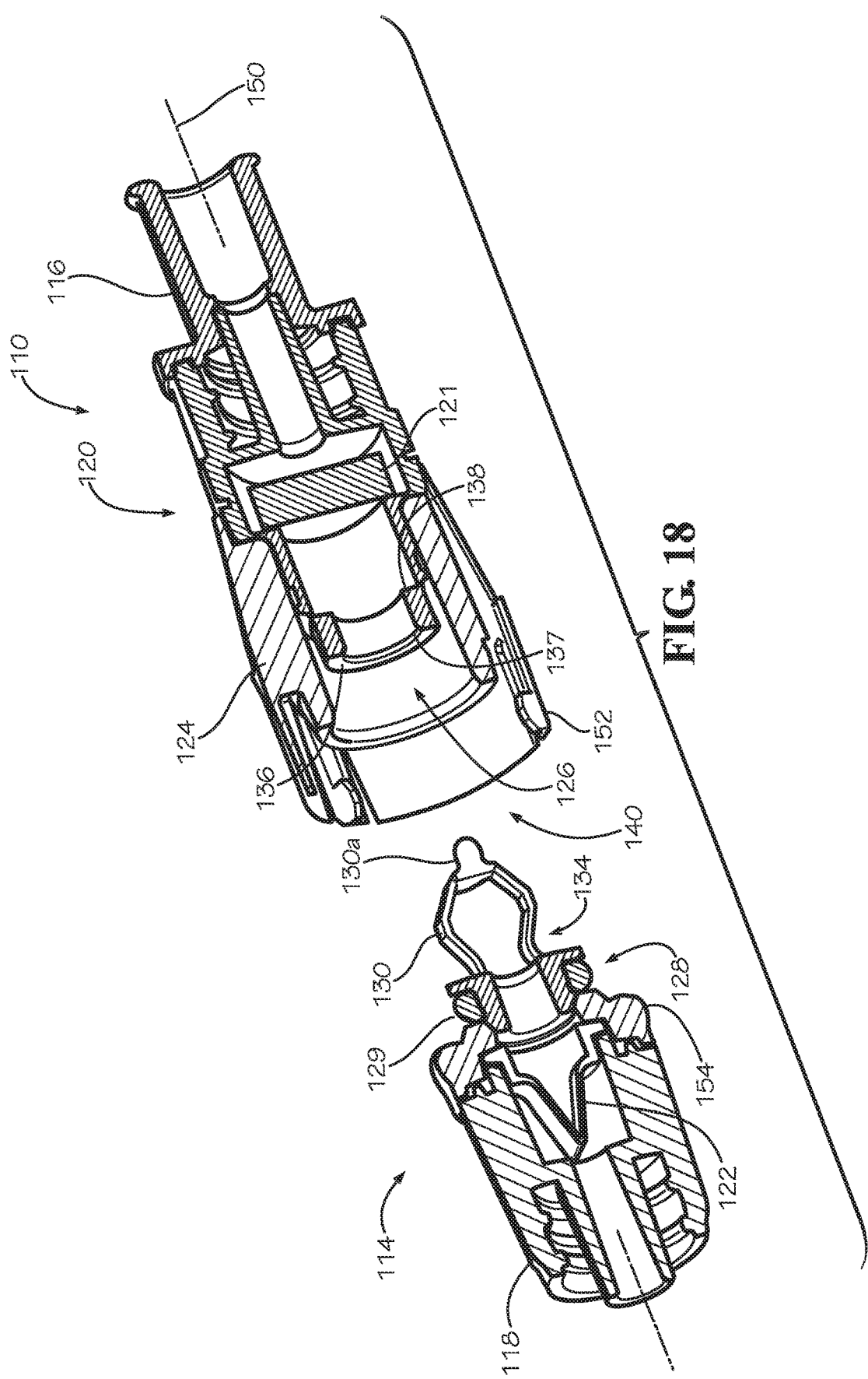
FIG. 18 is a partial exploded perspective view of an embodiment of a connector of the present disclosure.

Also seen in FIGS. 17 and 18, a first valve 120 is disposed on first or second member 112, 114. First valve 120 is shown on first member 112 in FIG. 18. When the male portion 128 of second member 114 is fully seated in socket 126, stem 130 engages the first valve and opens the first valve to allow flow between the first and second members 112, 114 through axial passage 140. This occurs when first end 130a of stem 130 contacts a portion of first valve 120 and opens first valve 120 in some embodiments. For example, as seen in FIG. 18, first valve 120 includes a check valve having a pusher 121. First valve 120 is naturally biased in a closed position when pusher 121 is positioned axially toward the second member 114. When first and second members 112, 114 are joined, stem 130 presses axially against pusher 121, causing first valve 120 to open, allowing flow of fluid to travel through axial passage 140 from first member 112 toward second member 114. If the valve 110 is inadvertently separated by a patient or other tension event, stem 130 is axially released from pusher 121, causing first valve 120 to resume its bias toward a closed position.

As seen in FIG. 18, in some embodiments a second valve 122 is positioned on second member 114. Second valve 122 is a check valve in some embodiments, and includes a duckbill check valve in additional embodiments. Second valve 122 is positioned to allow flow in the axial direction from first member 112 toward second member 114, but to block flow in the opposite axial direction. As such, if the valve 110 is separated such that first member 112 is disjoined from second member 114, then second valve 122 prevents flow from that side of the valve from flowing out of the free end of second member 114. Similarly, first valve 120 is operable to prevent flow from the first member side from flowing out of the free end of first member 112.

In some embodiments, first member 112 includes a pressure-actuated or luer-actuated first valve 120 such as those manufactured by NP Medical of Clinton, Mass. The first valve 120 may be an off-the-shelf component that is naturally biased in a closed position. First valve 120 in such configurations may be oriented such that the pusher member 121 is biased in a closed position toward the second member 114. When the stem 130 contacts the valve 120, the valve is temporarily opened during contact, allowing fluid or gas to move through the valve 120. When the contact by the stem 130 is removed, the valve 120 returns to its closed position automatically.

Referring further to FIG. 17, stem 130 in some embodiments is a frangible stem that is breakable when the first and second members 112, 114 are axially pulled apart. As such, stem 130 may be broken in a manner that prevents stem 130 from being operable to engage first valve 120 in the event first and second members 112, 114 are put back together. More specifically, frangible stem 130 is inoperable to open the first valve 120 to allow flow between the first and second members 112, 114 through the axial passage 140 when the frangible stem 130 is broken. If a user were to attempt to re-attach first and second members 112, 114 following a breakaway event, then no flow would be allowed to pass through axial passage 140 between first and second members 112, 114 in such embodiments.

As shown in FIG. 17, stem 130 includes a plurality of frangible bridges 132 in some embodiments. Each frangible bridge 132 extends from male portion 128 axially toward first member 112. Each frangible bridge 132 has a body that extends radially away from the centerline of the axial passage. As such, stem 130 defines a stem recess 134, shown in FIG. 18. Stem recess includes an axisymmetric radial depression located on the axial side of stem 130 away from first member 112. In some embodiments, first valve 120 includes a stem receiver 136 shaped to receive a portion of stem 130. Stem receiver 136 defines an axial passage in some embodiments, as seen in FIG. 18. Each frangible bridge 132 is radially resilient across a predetermined range of deflection in some embodiments. When stem 130 is inserted into the stem receiver 136, each frangible bridge 132 may be temporarily radially deflected toward the centerline axis 150 of the axial passage, shown in FIG. 19. As the stem 130 moves farther into the stem receiver 136 toward the pusher 121, the stem receiver 136 becomes axially aligned with the stem recess 134 and becomes seated in the stem recess 134. In some embodiments, the stem receiver 136 includes an outer opening facing toward second member 114. Outer opening edge 137 includes a beveled edge, as shown in FIG. 18 in some embodiments. The beveled edge of outer opening 137 allows frangible bridges 132 to be radially compressed without causing fracture of the bridges when stem 130 is inserted into the stem receiver 136. Additionally, stem receiver 136 includes an inner opening edge 138 in some embodiments. Inner opening edge 138 includes a square edge in some embodiments. When stem 130 is pulled from stem receiver 136 in the axial direction away from first member 112 during a breakaway event, stem receiver 136 becomes unseated from stem recess 134, and frangible bridges 132 are suddenly compressed radially inwardly by inner opening edge 138 on stem receiver 136. This interaction may cause one or more frangible bridges 132 on stem 130 to irreversibly fracture. This type of interaction resulting in breakage of one or more structural features on stem 130 provides a feature that prevents the connector 110 from being operable re-connected after a breakaway event.

Figure 19:
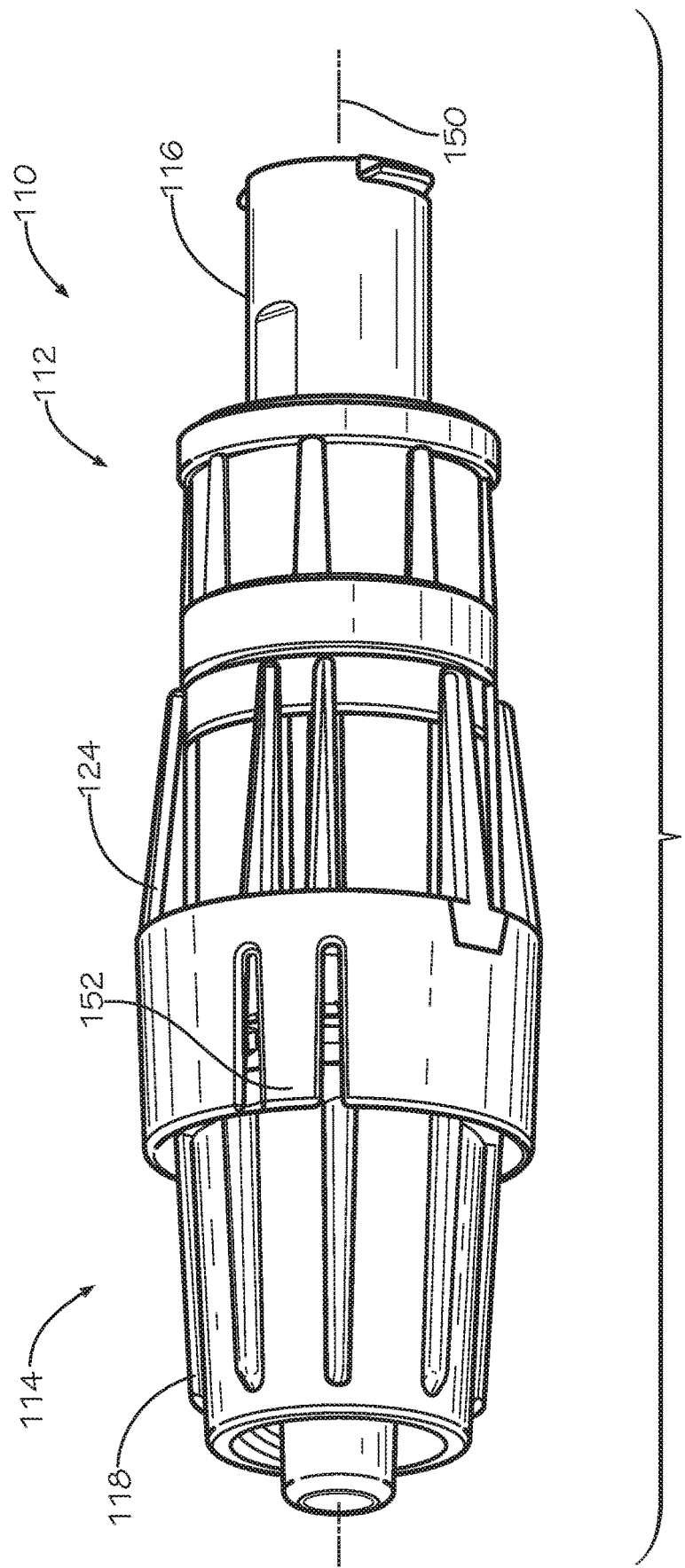
FIG. 19 is a perspective view of an embodiment of a connector of the present disclosure.

Referring further to FIGS. 18 and 19, in some embodiments the first and second members 112, 114 are held in axial alignment relative to each other by one or more mechanical interactions. For example, as shown in FIG. 18, housing 124 includes an outer shell having one or more housing clasps 152 extending toward second member 114. Each housing clasp 152 presses against the outer surface of second member 114 when first and second members are installed together. Second member 114 includes a detent ridge 154 in some embodiments, forming a slight protrusion radially outwardly from the body of the second member 114. Each housing clasp 152 slides over the detent ridge 154 when first and second members 112, 114 are joined together. The force between each housing clasp 152 and detent ridge 154 provides axial resistance when first and second members 112, 114 are pulled axially away from each other, such as during a breakaway event. By adjusting the mechanical fit between detent ridge 154 and housing clasps 152, the device 110 may be tuned to achieve a desired tensile separation force between first and second members 112, 114. Additionally, a secondary connection between male portion 128 and socket 126 also provides a component of the tensile force parameter in some embodiments. Thus, the interference fit between male portion 128 and the engagement between housing clasps 152 and detent ridge 154 provide the friction necessary to achieve a desired tensile force in some applications.

Thus, although there have been described particular embodiments of the present disclosure of a new and useful BREAKAWAY CONNECTOR, it is not intended that such references be construed as limitations upon the scope of this disclosure.

What is claimed is:

1. A connector apparatus for joining a first tubing section to a second tubing section, the apparatus comprising:
   a first member including a housing clasp extending from the first member;
   a second member positioned axially opposite the first member, the second member including a male portion extending from the second member, and the second member including a detent ridge forming a protrusion radially outwardly from the second member;
   a housing disposed between the first and second members, the housing including a socket shaped to receive the male portion of the second member;
   an axial passage providing a flow path defined inside the housing between the first and second members;
   a stem disposed in the axial passage between the first and second members;
   a first valve disposed on the first member, wherein the first valve is a check valve; and
   a second valve disposed on the second member, wherein the second valve is a check valve,
   wherein the housing clasp slides over the detent ridge and applies force against the detent ridge when the first and second members are joined together,
   wherein the force between the housing clasp and the detent ridge provides axial resistance between the first and second members when the first and second members are pulled axially away from each other,
   wherein the first and second members do not separate until a threshold tensile force is applied between first and second members when the first and second members are pulled axially away from each other,
   wherein the stem engages the first valve and opens the first valve and the stem engages the second valve and opens the second valve to allow flow between the first and second members through the axial passage when the male portion of the second member is fully received in the socket of the housing,
   wherein the stem is frangible, and the frangible stem is configured to irreparably break into at least two portions when the first and second members are axially pulled apart.

2. The apparatus of claim 1, further comprising a seal on the male portion of the second member.

3. The apparatus of claim 2, further comprising a first fitting disposed on the first member.

4. The apparatus of claim 3, further comprising a second fitting disposed on the second member.

5. The apparatus of claim 4, wherein the second valve is a duckbill check valve.

6. The apparatus of claim 5, wherein the frangible stem is inoperable to open the first valve to allow flow between the first and second members through the axial passage when the frangible stem is broken.

7. The apparatus of claim 6, further comprising an interference fit between the male portion of the second member and the socket of the housing.

8. The apparatus of claim 7, wherein the housing is fixed to the first member.

9. The apparatus of claim 8, wherein the first valve is naturally biased in a closed position.

10. A connector apparatus for joining a first tubing section to a second tubing section, the apparatus comprising:
- a first member including a housing clasp extending from the first member, the first member defining an open socket axially spaced from the housing clasp;
- a second member positioned axially opposite the first member, the second member including a male portion extending from the second member, and the second member including a detent ridge forming a protrusion radially outwardly from the second member axially spaced from the male portion, wherein the male portion is dimensioned to fit in the open socket in an interference fit;
- an axial passage providing a flow path between the first and second members defined inside the male portion;
- a stem disposed in the axial passage between the first and second members,
- wherein the stem is configured to be either broken into at least two pieces or irreversibly deformed, preventing re-connection when the first and second members are axially separated;
- a first valve disposed on the first member, wherein the first valve is a check valve; and
- a second valve disposed on the second member, wherein the second valve is a check valve,
- wherein the housing clasp slides over the detent ridge and applies force against the detent ridge when the first and second members are joined together,
- wherein the force between the housing clasp and the detent ridge provides a first component of axial resistance between the first and second members when the first and second members are pulled axially away from each other,
- wherein the interference fit between the male portion and the socket provides a second component of axial resistance between the first and second members when the first and second members are pulled axially away from each other,
- wherein the first and second members do not separate until a threshold tensile force sufficient to overcome the combined first and second components of axial resistance is applied between first and second members,
- wherein when the male portion of the second member is fully received in the socket of the housing the stem engages the first valve and opens the first valve and the stem engages the second valve and opens the second valve to allow flow between the first and second members through the axial passage.

11. The apparatus of claim 10, wherein the second check valve is a duckbill valve.

12. The apparatus of claim 11, further comprising an o-ring disposed on the male portion.

13. The apparatus of claim 12, wherein radial compression of the o-ring inside the socket provides the interference fit between the male portion and the socket.

14. The apparatus of claim 10, wherein the stem is configured to irreparably break into at least two pieces, and breakage of the stem provides a third component of axial resistance, wherein the first and second members do not separate until a threshold tensile force sufficient to overcome the combined first, second and third components of axial resistance is applied between first and second members.

* * * * *